United States Patent [19]  [11] 4,021,446
Fischli et al.  [45] May 3, 1977

[54] 4-BENZYLOXYMETHYL-5-[(1-PYRROLIDINYL-CARBONYL)-METHYL]-1,3-CYCLOPENTYLENE-DIACETATE COMPOUNDS

[75] Inventors: Albert Eduard Fischli, Basel, Switzerland; Michael Josef Klaus, Weil am Rhine, Germany; Hans Johann Mayer, Fullinsdorf; Alexander Eduard Wick, Riehen, both of Switzerland

[73] Assignee: Hoffmann-La Roche Inc., Nutley, N.J.

[22] Filed: Oct. 9, 1975

[21] Appl. No.: 620,990

Related U.S. Application Data

[62] Division of Ser. No. 389,756, Aug. 20, 1973, Pat. No. 3,929,853.

[30] Foreign Application Priority Data

Aug. 28, 1972 Switzerland .................... 12684/72
July 12, 1973 Switzerland .................... 10165/73

[52] U.S. Cl. ................. 260/326.4; 260/247.7 P; 260/293.56; 260/326.5 C; 260/343.2 R; 260/343.3 R; 260/345.8; 260/345.9; 250/346.3; 260/346.8 R; 260/464; 260/468 L; 260/468 D; 260/456 R; 260/473 R
[51] Int. Cl.² ............................... C07D 207/06
[58] Field of Search .................. 260/326.4, 326.46

[56] References Cited

UNITED STATES PATENTS 3,929,853  12/1975  Fischli et al. ............. 260/326.5 C

OTHER PUBLICATIONS

Corey et al., J.A.C.S., vol. 92, p. 397, (1970).
Corey et al., J.A.C.S., vol. 93, pp. 1490–1491, (1971).

*Primary Examiner*—Donald G. Daus
*Assistant Examiner*—Mary C. Vaughn
*Attorney, Agent, or Firm*—Samuel L. Welt; Bernard S. Leon; Richard A. Gaither

[57] ABSTRACT

A process for preparing (3,4,5,6)-4-benzyloxymethyl-hexahydro-5-hydroxy-2H-cyclopenta[b]furan-2-one, a known intermediate for producing prostaglandins from 5,6-dimethylbicyclo[2.2.1]hept-5-en-2-endo-3-endo-dicarboxylic acid anhydride and intermediates in this process.

2 Claims, No Drawings

4-BENZYLOXYMETHYL-5-[(1-PYRROLIDINYL-CARBONYL)-METHYL]-1,3-CYCLOPENTYLENE-DIACETATE COMPOUNDS

This is a division of application Ser. No. 389,756 filed Aug. 20, 1973, entitled PREPARATION OF CYCLOPENTANE DERIVATIVES, now U.S. Pat. No. 3,929,853.

SUMMARY OF THE INVENTION

In accordance with this invention, a stereospecific method is provided for synthesizing a compound of the formula:

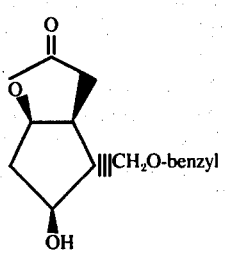

XV or enantiomers or racemates thereof from a 5,6-dimethylbicyclo [2.2.1]hept-5-en-2-endo-3-endo-dicarboxylic acid anhydride having the formula:

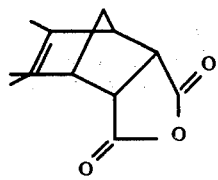

II via an intermediate of the formula:

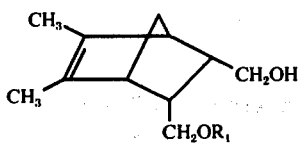

I wherein $R_1$ is hydrogen or a radical derived from an optically active or inactive aromatic or aliphatic dicarboxylic acid by removal of the hydrogen from one of the carboxyl groups, a radical derived from an optically active aliphatic or araliphatic monocarboxylic acid by removal of the hydrogen of the carboxyl group, a radical derived from an optically active sulfonic acid by removal of the hydrogen of the sulfanoyl group and the radical derived from an optically active carbamic acid by removal of the hydrogen from the carbamoyl group.

The compound of formula XV and racemates thereof are known intermediates for prostaglandins such as prostaglandin $F_{2\alpha}$ and $E_2$, as disclosed in J. Am. Chem. Soc. 91, 5675; J. Am. Chem. Soc. 92, 397; and J. Am. Chem. Soc. 93, 1490–1. The conversion of the compounds of formula XV, its enantiomer or its racemates is to prostaglandins $F_{2\alpha}$ and $E_2$ and their enantiomers is carried out by the procedures given in J. Am. Chem. Soc. 91, 5675; J. Am. Chem. Soc. 92, 397; and J. Am. Chem. Soc. 93, 1490–1.

The enantiomer of the compound of formula XV has the formula:

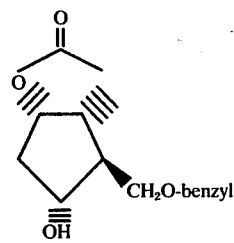

XV-A

In accordance with this invention, a process is provided for stereospecifically producing either the compound of formula XV or its enantiomer, i.e., the compound of formula XV-A or racemates thereof from the compound of formula II. The compounds of formula XV or XV-A can be produced in accordance with this invention in their optically active forms or as racemates thereof.

DETAILED DESCRIPTION OF THE INVENTION

In the pictorial representation of the compounds given throughout this application, a thickened tapered line (▼) indicates a substituent which is in the beta-orientation (above the plane of the cyclopentane moiety) and a barred line (≡) indicates a substituent which is in the alpha-orientation (below the plane of the cyclopentane moiety). It is to be understood that the pictorial representations of the structural formula represent absolute configuration unless otherwise stated. In many cases, for sake of convenience, only one optically active antipode is pictorially represented. It is understood that each pictorial representation designates either or both optically active antipodes.

The optically inactive dicarboxylic acids which can form the residue $R_1$, can be any conventional monocyclic, bicyclic or tricyclic aromatic dicarboxylic acid containing from 8 to 20 carbon atoms such as phthalic acid, isophthalic acid and teraphthalic acid. The optically inactive aliphatic dicarboxylic acid can be any conventional saturated or unsaturated aliphatic dicarboxylic acid containing from 3 to 12 carbon atoms. Among the preferred optically inactive dicarboxylic acids are included oxalic acid, succinic acid, fumaric acid, etc. $R_1$ can also be the residue of any conventional mono- or dicarboxylic acids such as optically active aliphatic monocarboxylic acids, optically active araliphatic acids, optically active aromatic acids. Any conventional optically active carboxylic acids commonly utilized to resolve alcohols can be utilized in forming the substituent $R_1$. Examples of optically active monocarboxylic acids are aliphatic, araliphatic and aromatic monocarboxylic and dicarboxylic acids such as D-tartaric acid, L-tartaric acid, menthoxyacetic acid and aeticholenic acid. Any conventional optically active sulfonic acid which is commonly employed to resolve alcohols can be utilized to form the substituent $R_1$. Among the preferred optically active sulfonic acids is camphorsulfonic acid. Any conventional optically active carbamic acid which is utilized for resolving alcohols can be utilized to form the substituent $R_1$. Among the preferred optically active carbamic acids are dehydroabietyl-carbamic acids, isobornylaminocarbamic acid.

The term "halogen" includes all four halogens, such as bromine, chlorine, fluorine and iodine. The term "lower alkyl" as utilized throughout this application designates lower alkyl groups containing from 1–7 carbon atoms such as methyl, ethyl, n-propyl, isopropyl, etc.

In the first step of the process of this invention, the compound of formula II is treated with a reducing agent to form a compound of the formula:

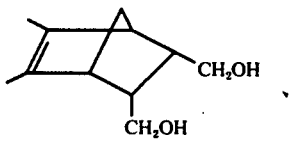

In carrying out this reaction, any conventional reducing agent which will reductively open an anhydride ring can be utilized. Among the preferred reducing agents are the complex metal hydride reducing agents such as lithium aluminum hydride, sodium borohydride or lithium borohydride, diborane or an alkali metal such as sodium or lithium in ammonia. This reduction can be carried out directly or stepwise, that is to say, via the lactone or the hydroxy carboxylate depending upon the type of reducing agent and conditions employed. Any of the conditions conventional in utilizing these types of reducing agents can be utilized in carrying out the conversion of the compound of the formula II to a compound of the formula Ia.

The compound of formula Ia can be converted into a compound of the formula:

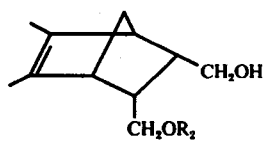

wherein $R_2$ is a radical derived from an optically active or optically inactive aromatic or aliphatic dicarboxylic acid by removal of the hydrogen from one of the carboxyl groups, a radical derived from an optically active aliphatic or araliphatic monocarboxylic acid by removal of the hydrogen of the carboxyl group, a radical derived from an optically active sulfonic acid by removal of the hydrogen of the sulfanoyl group or the radical derived from an optically active carbamic acid by removal of the hydrogen from the carbamoyl group, by esterification.

Any conventional method of esterification can be utilized to convert the diol of formula Ia to the ester of formula Ib. For example, the esterification of the diol of formula Ia can be carried out by reaction with a calculated amount of an appropriate acid derivative (e.g., an acid anhydride or acid halide). For the manufacture of carbamic acid esters, there can be utilized isocyanates such as methyl isocyanate or phenethylamino isocyanate. Carbamic acid esters can also be manufactured by reacting the diol with an equimolar amount of phosgene and subsequent reaction of the resulting chlorocarbonic acid ester with an amine (e.g., isobornyl amine).

If the diol is esterified with an optically active acid or a reactive derivative thereof, or an optically active isocyanate, the hemi-ester is obtained as a diastereomer pair which can be separated by conventional procedures such as crystallization or chromatography. If an optically inactive dicarboxylic acid is used in the esterfication, the hemi-ester is obtained as a racemate which can be converted by reaction of the free carboxyl group with an optically active base into a diastereomer pair which can be separated by conventional physical methods. Undesired diastereomers obtained in this manner can be reconverted into the diol by saponification. Therefore, if desired, the compound of formula I can be converted into its optically active form. On the other hand, the compound of formula I can be utilized as a racemate. In accordance with this invention, the optical configuration of formula I is carried throughout this process so as to prepare the compound of formula XV or XV-A having the same optical configuration. On the other hand, if the compound of formula I is in the form of a racemate, this racemate can be converted to the compound of formula XV or XV-A to produce the compound of formula XV or formula XV-A in the form of a racemate.

In accordance with one embodiment of this invention, the compound of formula Ib is converted to the compound of formula XV. In the first step of this conversion, the compound of formula Ib is oxidized to form a compound of the formula:

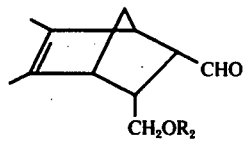

wherein $R_2$ is as above.

In the next step of this process, the compound of formula III above is converted into an enol acetate of the formula:

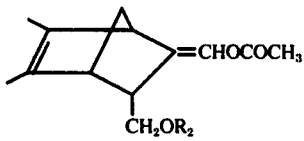

wherein $R_2$ is as above.

The enol acetate of formula IV is then saponified to give an aldehyde of the formula:

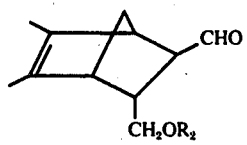

wherein $R_2$ is as above.

On the other hand, the compound of formula III can be converted directly into an aldehyde of formula V by heating to a temperature of from 50° C. to 120° C. with a secondary amine such as piperidine, pyrrolidine, morpholine or a di(lower alkyl)amine such as di(n-butyl)amine, to give the aldehyde of formula V. The aldehyde of formula V is next reduced to give an alcohol of the formula:

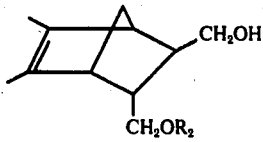

wherein R₂ is as above. The alcohol of formula VI is converted by conventional etherification into a tetrahydropyranyl ether of the formula:

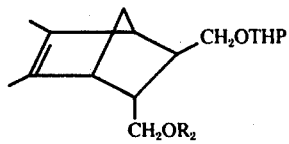   VII wherein R₂ is as above, and THP is tetrahydropyranyl.

In the next step, the ester group R₂ in a tetrahydropyranyl ether of formula VII is saponified by conventional means to form a compound of the formula:

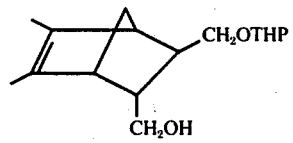   VIII wherein THP is as above. The compound of formula VIII is esterified with a reactive derivative of a sulfonic acid of the formula R₃OH, in which R₃ is a lower alkylsulfonyl or arylsulfonyl group, to give a compound of the formula:

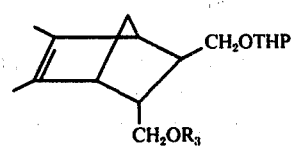   IX wherein R₃ and THP are as above. The lower alkylsulfonyls are those alkylsulfonyls where the lower alkyl group contains from 1 to 6 carbon atoms. The arylsulfonyls are those arylsulfonyls where the aryl group is preferably phenyl or lower alkyl or halo substituted phenyl where lower alkyl is defined as above.

The compound of formula IX is reacted with sodium cyanide in dimethyl sulfoxide to give a compound of the formula:

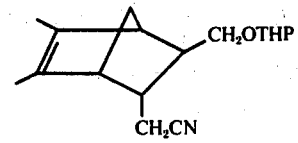   X wherein THP is as above. The ether group in a compound of formula X is cleaved off by conventional ether hydrolysis to form a compound of the formula:

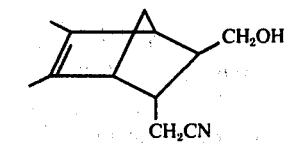   XI

The compound of formula XI can be converted into the benzyl ether of the formula:

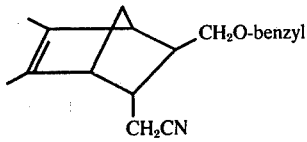   XII by conventional etherification.

In the next step, the benzyl ether of formula XII is subjected to ozone to form an ozonide.

The ozonide is reduced to form a cyclopentane derivative of the formula:

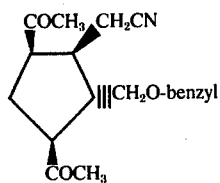   XIII or the racemate thereof.

The compound of formula XIII or its racemate is treated with trifluoroperacetic acid and disodium hydrogen phosphate in methylene chloride to form a cyclopentane derivative of the formula:

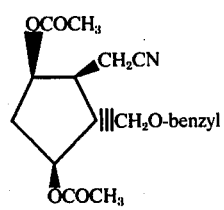   XIV or the racemate thereof which is then converted into a cyclopentane derivative of formula XV or the racemate thereof by treatment with alcoholic potassium hydroxide.

The oxidation of a compound of formula Ib can be carried out, for example, according to the Pfitzner-Moffatt method using dimethyl sulfoxide in the presence of phosphoric acid and dicyclohexylcarbodiimide or with pyridine/SO₃. Any of the conditions conventional in Pfitzner-Moffatt oxidation can be utilized in carrying out this reaction. The free carboxyl group in a compound of formula Ib can be expediently converted into an ester group prior to the oxidation.

The enolacetylation of a compound of formula III can be carried out by reacting with a reactive derivative of acetic acid by conventional means such as by treatment with acetic anhydride and sodium acetate at 155° C. (reaction time about 3 hours).

An enol acetate of formula IV can be saponified such as by treatment with piperidine in an inert organic solvent such as methanol for 1.5 hours at 70° C. to give an aldehyde of formula V. Any conventional method of saponifying an enol acetate using basic conditions can be used in carrying out this reaction.

The reduction of an aldehyde of formula V to give an alcohol of formula VI can be carried out using sodium borohydride in methanol.

From an alcohol of formula VI there can be obtained, by treatment with dihydropyran in the presence of a catalytic amount of acid, a tetrahydropyranyl ether of formula VII.

A tetrahydropyranyl ether of formula VII can be saponified by conventional means such as by treatment with methanolic potassium hydroxide to give the alcohol of formula VIII.

By reaction with an appropriate sulfonyl chloride, an alcohol of formula VIII can be converted into a sulfonic acid ester of formula IX.

The nitrile of formula X can be obtained by heating a compound of formula IX for 14 hours with sodium cyanide in dimethyl sulfoxide at 100° C.

The cleavage of the tetrahydropyranyl ether group in the nitrile of formula X can be carried out using acids in methanolic solution by conventional procedures. There is thus obtained a compound of formula XI.

The benzyl ether of formula XII can be obtained from the compound of formula XI by treatment with benzyl chloride in dimethoxyethane in the presence of sodium hydride at 80° C.

The ozonization of the benzyl ether of formula XII can be carried out by treatment with ozone utilizing conventional procedures. In carrying out this reaction, temperatures of −100° to 20° C. can be utilized. This reaction can take place in a conventional inert organic solvent such as ethyl acetate, etc.

The reduction of the ozonide can be carried out by catalytic hydrogenation. Any conventional means of catalytic hydrogenation can be utilized. Among the preferred catalysts are included noble metal catalysts such as palladium and platinum with palladium on carbon being preferred. In carrying out this hydrogenation, temperatures of from −100° to 20° C are preferred.

On the other hand, the reduction of the ozonide of formula XII-B can be carried out by treatment with dimethyl sulfide. In carrying out this reduction, temperatures of from −100° to 20° C. can be utilized. If desired, this reaction can take place in a conventional inert organic solvent. Any conventional inert organic solvent can be utilized in carrying out this reaction. There is thus obtained a cyclopentane derivative of formula XIII.

By reacting the cyclopentane derivative of formula XIII with trifluoroperacetic acid in the presence of disodium hydrogen phosphate in methylene chloride at room temperature there is obtained the diacetate of formula XIV. The diacetate of formula XIV can be saponified with methanolic potassium hydroxide to give the cyclopentane derivative of formula XV.

The compound of formula Ib is converted to the compound of formula XV-A by first converting the compound of formula Ib to a compound of the formula:

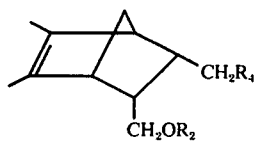 XVI wherein $R_2$ is as above; and $R_4$ is sulfonyloxy derived from an organic sulfonic acid or chlorine, bromine or iodine.

In the next step, the $R_4$ group in a compound of formula XVI is replaced by a nitrile group to obtain a compound of the formula:

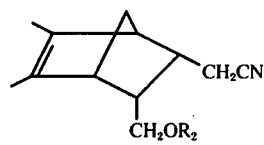 XVII wherein $R_2$ is as above.

The compound of formula XVII is converted into a lactone of the formula:

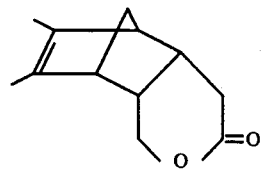 XVIII by treatment with alkali. The lactone of formula XVIII is reacted with a primary or secondary amine to give a compound of the formula:

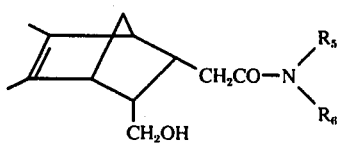 XIX wherein $R_5$ and $R_6$ are hydrogen or lower alkyl or $R_5$ and $R_6$ taken together with their attached nitrogen form a heterocyclic ring which may contain at most one additional oxygen or nitrogen hetero atom.

The compound of formula XIX is oxidized to give a compound of the formula:

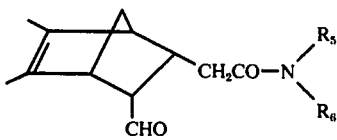 XX wherein $R_5$ and $R_6$ are as above.

The compound of formula XX is rearranged by heating the compound of formula XX to a temperature of from 50° C. to 120° C. in the presence of a secondary amine to produce a compound of the formula:

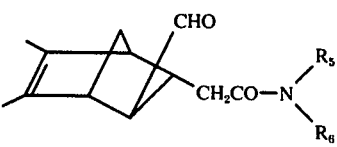 XXI wherein $R_5$ and $R_6$ are as above. The same secondary amines described in connection with the conversion of a compound of formula III to a compound of formula V can be utilized in carrying out this reaction.

The compound of formula XXI is reduced to a compound of the formula:

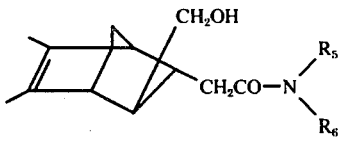

XXII where $R_5$ and $R_6$ are as above. The free hydroxy group in the compound of formula XXII is then esterified with an activated benzyl alcohol derivative such as benzyl chloride to form the benzyl ether of formula:

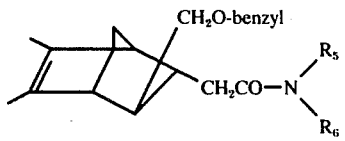

XXIII

The compound of formula XXIII is then treated with ozone in the manner described in connection with the ozonolysis of a compound of the formula XII to form an ozonide. The ozonide is then treated with a reducing agent in the manner described in connection with the reduction of the compound of formula XII-B to form a compound of the formula:

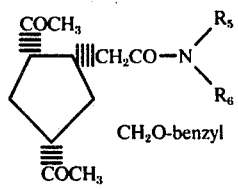

XXIV wherein $R_5$ and $R_6$ are as above;
or a racemate thereof. The compound of formula XXIV or a racemate thereof is treated with trifluoroperacetic acid and disodium hydrogen phosphate in methylene chloride to obtain a cyclopentane derivative of the formula:

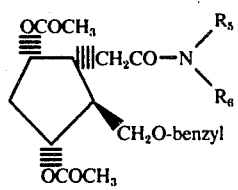

XXV or a racemate thereof which is converted by treatment with alcoholic alkali metal hydroxide solution into a cyclopentane derivative of the formula:

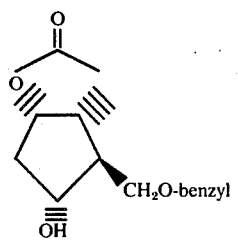

XV-A or a racemate thereof.

The conversion of the hydroxy group in a compound of formula Ib into the group $R_4$ can be carried out by conventional procedures, for example, by reaction with a sulfonyl halide or an appropriate phosphorous halide.

Among the preferred sulfonyloxy groups are lower alkylsulfonyloxy, phenylsulfonyloxy, or halo or lower alkyl substituted phenylsulfonyloxy with mesyloxy, tosyloxy and brosyloxy (0-bormophenylsulfonyloxy) being especially preferred.

The replacement of the $R_4$ group in a compound of formula XVI thus obtained by the nitrile group can be carried out by treatment with an alkali metal cyanide (e.g., sodium cyanide) or an alkaline earth metal cyanide in an aprotic polar solvent such as dimethyl sulfoxide.

A thus obtained compound of formula XVII can be converted into the lactone of formula XVIII by conventional means, for example, by using aqueous-alcoholic potassium hydroxide.

The lactone of formula XVIII is then converted into a compound of formula XIX by reaction with an appropriate primary or secondary amine. Especially suitable amines are cyclic or acyclic amines such as, for example, pyrrolidine, piperidine, morpholine or mono or di(lower alkyl) substituted amines such as methyl amine, ethyl amine or di(n-butyl amine).

The oxidation of a compound of formula XIX to give a compound of formula XX can expediently be carried out according to the Pfitzner-Moffatt method or using pyridine/$SO_3$ in the same manner as described in connection with the oxidation of a compound of formula Ib to a compound of formula II.

Suitable secondary amines which may be used in the rearrangement of a compound of formula XX to a compound of formula XXI are those mentioned earlier in connection with the conversion of the lactone of formula XVIII into a compound of formula XIX. The rearrangement is expediently carried out in a solvent such as benzene at a temperature between 50° C. to 120° C. However, any conventional inert organic solvent can be utilized to carry out this rearrangement.

Especially suitable reducing agents for the reduction of the aldehyde group in a compound of formula XXI are complex metal hydrides such as sodium borohydride, lithium borohydride, lithium aluminum hydride and Redal [$NaH_2Al(OC_2H_5OCH_3)_2$].

The following examples are illustrative but not limitative of this invention. All temperatures utilized in these examples are in degrees centigrade and the ether is diethyl ether. The term "dilute hydrochloric acid" denotes an 0.001 to 3.0 N aqueous solution of hydrochloric acid. The term "concentrated hydrochloric acid" denotes an aqueous solution containing 37% by weight of hydrochloric acid.

EXAMPLE 1

12.7 g of lithium aluminum hydride were suspended in 600 ml of absolute diethyl ether. After cooling to 0° C, a solution of 40.5 g of 5,6-dimethylbicyclo[2.2.1-]hept-5-en-2-endo, 2-endo-dicarboxylic acid anhydride in 220 ml of absolute diethyl ether was slowly added dropwise with stirring and stirred overnight at room temperature. With cooling with an ice-bath, a mixture of 150 ml of tetrahydrofuran and 30 ml of water was allowed to drop in, the solution was then poured on to ice and dilute aqueous hydrochloric acid and stirred for a further 1 hour. The aqueous phase was separated, washed twice with diethyl ether and the combined ether solutions washed once with water, sodium bicarbonate solution and water. After drying over sodium sulphate and distillation of the solvent, there were obtained 30 g of 5,6-dimethyl-bicyclo[2.2.1]hept-5-en-2-endo, 3-endo-dimethanol, which melted at 106°–107° C after recrystallization from ethyl acetate. IR: 3320, 3236, 1011 cm$^{-1}$ (solid in KBr).

EXAMPLE 2

5.4 g of 5,6-dimethyl-bicyclo[2.2.1]hept-5-en-2-endo, 3-endo-dimethanol were dissolved in 50 ml of pyridine, 4.8 g of finely powdered phthalic acid anhydride added and the mixture subsequently heated for 4 hours at 100° C. After cooling, the solution was poured on to ice and hydrochloric acid and extracted several times with ethyl acetate. The crystal mass remaining after evaporation of the solvent was dissolved in a solution of 4 g of sodium carbonate in 200 ml of water and extracted 3 times with ethyl acetate. From the organic phase 1.4 g of starting material could be recovered after evaporation. The aqueous phase was acidified with dilute aqueous hydrochloric acid, extracted with ethyl acetate, the organic phase dried over sodium sulphate and the solvent distilled off. The remaining crystalline product was recrystallized from isopropanol and gave 4.5 g of [3-endo-(hydroxymethyl)-5,6-dimethyl-5-norbornen-2-endo-yl]methylhydrogenphthalate of melting point 206°–208° C. IR: 3374, 2668, 1723 cm$^{-1}$ (solid in KBr).

EXAMPLE 3

1.0 g of 5,6-dimethyl-bicyclo[2.2.1]hept-5-en-2-endo, 3-endo-dimethanol was dissolved in 250 ml of absolute toluene and cooled to 0°–2° C with ice. 544 mg of phosgene dissolved in 10 ml of cold, absolute toluene were subsequently allowed to drop into the cold solution. The mixture was then stirred for 1 hour with external ice-cooling under a nitrogen atmosphere. The solution was mixed with 11.2 g of dry sodium carbonate and cooled for a further 0.5 hour with ice and stirred under nitrogen. Subsequently 1.01 g of natural [[a]$_D^{20}$ = −42.9° (c = 0.963 in rectified ethyl alcohol)] exo-bornylamine were added and the mixture stirred for a further hour with ice-cooling and then stirred vigorously for 2 hours at room temperature. After filtering off the solid constituents, 0.1-N aqueous hydrochloric acid was added and the product extracted from the mixture with ethyl acetate. After drying the organic phase with sodium sulphate and removing the solvent, there was obtained (3-endo-hydroxymethyl-5,6-dimethyl-5-norbornen-5-endo-yl)-methyl-(IR)-2-exo bornane-carbamate as a colorless oil, diastereomer mixture, [α]$_D^{22}$ = −25° (c = 1 in rectified alcohol).

EXAMPLE 4

60 g of the diastereomer mixture obtained according to Example 3 were dissolved in 166 ml of ethyl acetate and left to stand for 16 hours at room temperature. 24.7 g of crystals, which showed a rotation of [α]$_D^{22}$ = −31.2° (c = 1.0 in rectified alcohol), crystallized out of the solution. The crystals thus obtained were recrystallized with 155 ml of ethyl acetate, there being obtained 9.3 g of crystals with the rotation [α]$_D^{22}$ = −40.6° (c = 1.0 in rectified alcohol). A further recrystallization from 43 ml of ethyl acetate yielded 6.1 g of a crystallizate with a rotation of −56.2° (c = 1.0 in rectified ethyl alcohol). Further crystallizations no longer altered the rotation of the product. The melting point of the product was 157°–158° C.

EXAMPLE 5

83.1 g of the mother liquors obtained from the racemate clevage of Example 4 were dissolved with 250 g of potassium hydroxide in 1.6 liters of ethanol and 1.4 liters of water and boiled for 16 hours at reflux under nitrogen. The solution was cooled down and extracted three times with 2 liters of methylene chloride. The organic phase was extracted with 4 liters of 1.0-N aqueous hydrochloric acid to remove the isobornylamine. After removal of the solvent and crystallization, there was obtained 5,6-dimethyl-bicyclo[2.2.1]-hept-5-en-2-endo, 3-endo-dimethanol, which, after recrystallization from ethyl acetate, melted at 166°–167° C.

EXAMPLE 6

100 mg of [(IR)-3-endo-hydroxymethyl-5,6-dimethyl-5-norbornen-2-endo-yl](IR)-2-exo-bornane-carbamate obtained according to Example 4 were dissolved in 1 ml of absolute benzene and 1 ml of dimethylsulphoxide (distilled over calcium hydride). Subsequently the solution was mixed with 0.0224 ml of pyridine (as a 10% by weight solution in absolute benzene), 0.0106 ml of trifluoroacetic acid (as a 10% by weight solution in absolute benzene) and 172 mg of dicyclohexyl-carbodiimide. The reaction mixture was then stirred for 8 hours at room temperature. The suspension obtained was diluted with ethyl acetate and filtered. The organic solution was washed twice with water and the solvent evaporated. The residue was freed from excess dicyclohexylcarbodiimide on a silica gel column. Crystallization of the product from hexane yielded pure [(IR)-3-endo-formyl-5,6-dimethyl-5-norbornen-2-endo-yl]methyl(IR)-2-exo-bornane-carbamate with a melting point of 139°–141° C; [α]$_D^{22}$ = −20.5° (c = 1.0 in rectified alcohol).

EXAMPLE 7

1.0 g of [(IR)-3-endo-formyl-5,6-dimethyl-5-norbornen-2-endo-yl]methyl(IR)-2-exo-bornane-carbamate were dissolved in 3 ml of absolute acetic anhydride and boiled at reflux with 100 mg of anhydrous sodium acetate for 2 hours under argon. After cooling, the reaction mixture was mixed with an ice/water mixture. The aqueous suspension obtained was extracted with ethyl acetate and the organic phase was dried over sodium sulphate and evaporated down. The residue was chromatographed on a silica gel column. There was obtained [(IR)-3-acetoxymethylene-5,6-dimethyl-5-norbornen-2-endo-yl]methyl(IR)-2-exo-bornane-carbamate; [α]$_D^{22}$ = +16° (c = 1.0 in rectified alcohol).

EXAMPLE 8

40 mg of [(IR)-3-endo-formyl-5,6-dimethyl-5-norbornen-2-endo-yl]methyl(IR)-2-exo-bornane-carbamate were dissolved in 4 ml of absolute benzene, mixed with 3.3 mg of pyridine acetate and boiled at reflux for 2 hours under nitrogen. After cooling, the solution was diluted with ether and vigorously stirred at room temperature for 20 minutes with 20 ml of 1-N aqueous sulphuric acid. The organic phase was separated, washed with water, dried over sodium sulphate and evaporated down. Crystallization of the residue from hexane yielded [(IR)-3-exo-formyl-5,6-dimethyl-5-norbornen-2-endo-yl]methyl(IR)-2-exo-bornane carbamate, of melting point 72°–73° C; [α]$_D^{22}$ = −60° (c = 1.0 in rectified alcohol).

EXAMPLE 9

650 mg of [(1R)-3-acetoxymethylene-5,6-dimethyl-5-norbornen-2-endo-yl]methyl(1R)-2-exo-bornane-carbamate were dissolved in 6.5 ml of absolute methanol and mixed with 0.174 ml of piperidine. The solution was boiled at reflux for 1.5 hours under argon. The solvent was then evaporated and the residue taken up in diethyl ether and stirred vigorously for 2 minutes with 100 ml of 1-N aqueous sulphuric acid at room temperature. The organic phase was separated, washed with water, dried over sodium sulphate and evaporated down. The oily residue crystallized from hexane and yielded [(1R)-3-exo-formyl-5,6-dimethyl-5-norbornen-2-endo-yl]methyl(1R)-2-exo-bornane-carbamate, with a melting point of 72°–73° C; $[\alpha]_D^{22} = -60°$ ($c = 1.0$ in rectified alcohol).

EXAMPLE 10

2.8 g of [(1R)-3-exo-formyl-5,6-dimethyl-5-norbornen-2-endo-yl]methyl(1R)-2-exo-bornane-carbamate were dissolved in 33 ml of absolute isopropanol, mixed with 1.48 g of sodium borohydride and stirred for 1 hour at room temperature under nitrogen. The reaction mixture was cooled with ice, the excess sodium borohydride decomposed by the addition of 3-N aqueous acetic acid and subsequently buffered with sodium bicarbonate. The solution was extracted with ethyl acetate, the organic extract dried over sodium sulphate and the solvent evaporated. There was obtained [(1R)-3-exo-hydroxymethyl-5,6-dimethyl-5-norbornen-2-endo-yl]methyl(1R)-2-exo-bornane-carbamate; $[\alpha]_D^{22} = -52°$ ($c = 0.51$ in rectified alcohol).

EXAMPLE 11

8.66 mg of [(1R)-3-exo-hydroxymethyl-5,6dimethyl-5-norbornen-2-endo-yl]methyl(1R)-2-exo-bornane-carbamate were dissolved in 23 ml of methylene chloride, mixed with 2.26 ml of dihydropyran and 0.02 ml of trifluoroacetic acid and stirred for 5.5 hours at room temperature under nitrogen. The solution was then mixed with an aqueous sodium bicarbonate solution and extracted with methylene chloride. The organic phase was dried over sodium sulphate and potassium carbonate and evaporated down. There was obtained [(1R)-5,6-dimethyl-3-exo]-[(tetrahydro-2H-pyran-2-yl)-oxy]methyl-(5-norbornen-2-endo-yl)-methyl(1R)-2-exo-bornane-carbamate as an oil; $[\alpha]_D^{22} = -37°$, 1 ($c = 0.466$ in rectified alcohol).

EXAMPLE 12

783 mg of [(1R)-5,6-dimethyl-3-exo]-[(tetrahydro-2H-pyran-2-yl)-oxy]methyl-(5-norbornen-2-endo-yl)-methyl(1R)-2-exo-bornane-carbamate were dissolved with 19.8 g of potassium hydroxide in 17.5 ml of ethanol and 15 ml of water and boiled at reflux for 15 hours under nitrogen. The cooled solution was diluted with water and extracted several times with ether. The ethereal phase was washed with aqueous sodium bicarbonate solution and 3 times with aqueous sodium dihydrogenphosphate solution and dried over potassium carbonate. After evaporation of the solvent, there was obtained (1R)-5,6-dimethyl-3-exo-[(tetrahydro-2H-pyran-2-yl)-oxy]methyl-[5-norbornen-2-endo-methanol] as an oil.

EXAMPLE 13

318.5 mg of (1R)-5,6-dimethyl-3-exo-[(tetrahydro-2H-pyran-2-yl)-oxy]methyl-5-norbornen-2-endo-methanol were dissolved in 3 ml of absolute pyridine and cooled to 0° C. Subsequently 0.12 ml of methanesulphonic acid chloride were added and the mixture stirred for 16 hours at room temperature under nitrogen. The reaction mixture was diluted with ethyl acetate and washed with water. The organic phase was separated, dried over sodium sulphate and potassium carbonate and evaporated down. There was obtained (1R)-5,6-dimethyl-3-exo-[(tetrahydro-2H-pyran-2-yl)-oxy]methyl-5-norbornen-2-endo-yl-methyl-methane-sulphonate as an oil $[\alpha]_D^{22} = -22°$ ($c = 0.83$ in rectified alcohol).

EXAMPLE 14

500 mg of [(1R)-3-endo-hydroxymethyl-5,6-dimethyl-5-norbornen-2-endo-yl]methyl(1R)-2-exo-bornane-carbamate were dissolved in 2 ml of methylene chloride and cooled to 0° C. Then 1.12 ml of absolute pyridine and 0.21 ml of methanesulphonic acid chloride were added and the mixture stirred for 5 hours at 0° C under nitrogen. Subsequently the mixture was diluted with methylene chloride, washed with cold 1-N phosphoric acid and with aqueous sodium bicarbonate solution. The organic solution was dried over sodium sulphate and evaporated down. There was obtained (1R)-5,6-dimethyl-3-endo-[(methylsulphonyl)-oxy]-methyl-5-norbornen-2-endo-yl-methyl(1R)-2-exo-bornane-carbamate; $[\alpha]_D^{22} = -17.0°$ ($c = 0.83$ in rectified alcohol).

EXAMPLE 15

13.9 g of (1R)-5,6-dimethyl-3-endo-[(methylsulphonyl)-oxy]methyl-5-norbornen-2-endo-yl-methyl-(1R)-2-exo-bornane-carbamate in 134 ml of dimethyl sulphoxide were slowly added dropwise at 90° C to a suspension of 30.6 g of sodium cyanide in 62.5 ml of dimethyl sulphoxide (distilled over calcium hydride). The mixture was stirred vigorously for 48 hours at 90° C under nitrogen. After cooling, the mixture was dissolved in ethyl acetate and a small amount of water. The organic phase was separated, washed with a small amount of water, dried over sodium sulphate and evaporated down (finally under high vacuum at 60° C). There was obtained crude [(1R)-3-endo-cyanomethyl-5,6-dimethyl-5-norbornen-2-endo-yl]methyl(1R)-2-exo-bornane-carbamate as a yellow viscous oil. After purification on a silica gel column, there was obtained a product with a rotation of $[\alpha]_D^{22} = +9°$ ($c = 0.118$ in rectified alcohol).

EXAMPLE 16

7.7 g of [(1R)-3-endo-cyanomethyl-5,6-dimethyl-5-norbornen-2-endo-yl]methyl(1R)-2-exo-bornane-carbamate were dissolved with 233 g of potassium hydroxide in 153 ml of alcohol and 153 ml of water and boiled at reflux for 16 hours under nitrogen. After cooling, the solution was extracted twice with ether. The aqueous solution was made acidic with concentrated aqueous hydrochloric acid, saturated with sodium chloride and extracted with plenty of ethyl acetate. The ethyl acetate extract was dried over sodium sulphate and evaporated down. There was obtained (1S)-3-endo-hydroxymethyl-5,6-dimethyl-5-norbornen-2-endo-acetic acid lactone of melting point: 71°–73° C; $[\alpha]_D^{22} = -11.1°$ ($c = 0$ 0.541 in rectified alcohol).

EXAMPLE 17

1 g of (IS)-3-endo-hydroxymethyl-5,6-dimethyl-5n-norbornen-2-endo-acetic acid lactone was dissolved in 40 ml of pyrrolidine and boiled at reflux for 2.5 hours under nitrogen. The excess pyrrolidine was evaporated, the residue taken up in ethyl acetate, the ethyl acetate solution separated, extracted with 1-N aqueous phosphoric acid, washed with saturated sodium chloride solution, dried over over sodium sulphate and evaporated down. The remaining colorless oil was crystalized from ethyl acetate/hexane. There was obtained 1-[{(IS)-3-endo-hydroxymethyl-5,6-dimethyl-5-norbornen-2-endo-yl}-acetyl]-pyrrolidine of melting point 74°–76° C; $[\alpha]_D^{22} = -18°$ ($c = 0.102$ in methylene chloride).

EXAMPLE 18

3.9 g of 1-[{(IS)-3-endo-hydroxymethyl-5,6-dimethyl-5-norbornen-2-endo-yl}-acetyl]-pyrrolidine were dissolved in 40 ml of absolute dimethyl sulphoxide (distilled over calcium hydride) and subsequently mixed with 1.2 ml of pyridine, 726 mg of crystallized phosphoric acid (100% $H_3PO_4$) and 31.5 g of N-cyclohexyl-$N^1$-[2-(N-methyl-morpholino)-ethyl]-carbodiimide. The mixture was stirred vigorously for 5 hours, subsequently diluted with ethyl acetate and wshed three times with saturated sodium chloride solution. The organic phase was dried over sodium sulphate and evaporated down. The residue was crystallized with n-hexane. There was obtained 1[{(IS)-3-endo-formyl-5,6-dimethyl-5-norbornen-2-endo-yl}-acetyl]-pyrrolidine of melting point 73°–75° C; $[\alpha]_D^{22} = -12°$ ($c = 0.102$ in methylene chloride).

EXAMPLE 19

500 mg of 1-[{(IS)-3-endo-formyl-5,6-dimethyl-5-norbornen-2-endo-yl}-acetyl]-pyrrolidine were dissolved in 5 ml of absolute benzene, mixed with 137.5 mg of piperidine acetate and boiled at reflux for 6 hours under nitrogen. The solution was then cooled down, diluted with ethyl acetate and stirred vigorously at 0° C for 30 minutes with 1-N sulphuric acid. The organic phase was separated, washed with saturated sodium chloride solution, dried over sodium sulphate and evaporated down. The residue was crystallized from hexane and there was obtained 1-[{(IS)-3-exo-formyl-5,6-dimethyl-5-norbornen-2-endo-yl}-acetyl]-pyrrolidine of melting point 102°–104° C; $[\alpha]_D^{22} = +63°$ ($c = 0.10$ in methylene chloride).

EXAMPLE 20

1.14 g of 1-[{(IS)-3-exo-formyl-5,6-dimethyl-5-norbornen-2-endo-yl}-acetyl]-pyrrolidine were dissolved in 13.5 ml of absolute isopropanol and mixed with 605 mg of sodium borohydride. The suspension was then stirred for 2 hours at room temperature under nitrogen. The mixture was subsequently cooled to 0° C and 3-N aqueous acetic acid was slowly added dropwise in order to decompose the excess sodium borohydride. The acidic solution was mixed with ethyl acetate and buffered to pH 7.0 with sodium bicarbonate. The aqueous phase was extracted with ethyl acetate, the organic phases combined, washed with saturated sodium chloride solution, dried over sodium sulphate and evaporated down. There was obtained 1-[{(IS)-3-exo-hydroxymethyl-5,6-dimethyl-5-norbornen-2-endo-yl}-acetyl]-pyrrolidine as a colorless, viscous oil; $[\alpha]_D^{22} = -24°$ ($c = 0.063$ in methylene chloride).

EXAMPLE 21

714.3 mg of 1-[{(IS)-3-exo-hydroxymethyl-5,6-dimethyl-5-norbornen-2-endo-yl}-acetyl]-pyrrolidine were dissolved in 10 ml of absolute tetrahydrofuran and mixed with 3 ml of distilled benzyl chloride and 535 mg of sodium hydride (50% oil dispersion). The mixture was subsequently boiled at reflux for 6 hours under nitrogen. The cooled reaction mixture was mixed with an aqueous sodium dihydrogenphosphate solution and extracted several times with ethyl acetate. The organic phase was dried over sodium sulphate and evaporated down. The excess benzyl chloride was removed under high vacuum. The crude 1[{(IS)-3-exo-benzyloxy-methyl-5,6-dimethyl-5-norbornen-2-endo-yl}-acetyl]-pyrrolidine thus obtained was used in the next stage of the synthesis without further purification. For the analysis, a preparation purified by chromatography on silica gel showed a rotation of $[\alpha]_D^{22} = +34°$ ($c = 0.066$ in methylene chloride).

EXAMPLE 22

300 mg of { 1-[{(IS)-3-exo-benzyloxymethyl-5,6-dimethyl-5-norbornen-2-endo-yl}-acetyl]-pyrrolidine were dissolved in 20 ml of methylene chloride and mixed with 41 mg of ozone at −78° C. The faint blue solution was immediately vigorously flushed with argon and subsequently mixed with 2 ml of dimethyl sulphide at −78° C. The mixture was then stirred for 1 hour at −10° C and for a further 1 hour at room temperature. After evaporation of the solvent at 40° C, there was obtained crude 1[{(1R, 2R, 3R, 5S)-2-benzyloxymethyl-3,5-diacetyl-cyclopentyl}-acetyl]-pyrrolidine, which was further processed in this form. $[\alpha]_D^{22} = +12°$ ($c = 0.08$ in methylene chloride).

EXAMPLE 23

327 mg of 1[{(1R, 2R, 3R, 5S)-2-benzyloxymethyl-3,5-diacetylcyclopentyl}-acetyl]-pyrrolidine were dissolved in 13 ml of methylene chloride and vigorously stirred at room temperature with 12.1 g of anhydrous disodium hydrogenphosphate. To this suspension, cooled externally with ice to 0° C, a solution of trifluoroperacetic acid in methylene chloride was slowly added dropwise. The trifluoroperacetic acid/methylene chloride solution was manufactured as follows:

0.56 ml of 90% by weight hydrogen peroxide was mixed with 10.5 ml of methylene chloride and cooled to 0° C. 3.58 ml of trifluoroacetic anhydride were slowly added dropwise into the cold two-phase mixture. The mixture was then stirred for 10 minutes at room temperature.

After the dropwise addition of the reagent, the mixture was stirred at room temperature for 1 hour. The mixture was subsequently mixed with water, sodium bicarbonate and methylene chloride and shaken. After phase separation, the aqueous phase was extracted twice more with methylene chloride. The organic phases were then combined, washed with saturation aqueous sodium chloride solution, dried over sodium sulphate and evaporated down. The remaining oil could be directly further processed. For the analysis, the crude (1S, 3R, 4S, 5R)-4-benzyloxymethyl-5-[(1-pyrrolidinyl-carbonyl)-methyl]-1,3-cyclopentylenediacetate was purified on a silica gel column; $[\alpha]_D^{22} = -1°$ ($c = 0.066$ in methylene chloride).

EXAMPLE 24

227 mg of (1S, 3R, 4S, 5R)-4-benzyloxymethyl-5-[1-pyrrolidinyl-carbonyl)-methyl]-1,3-cyclopentylene-diacetate were dissolved with 6.2 g of potassium hydroxide in 15.5 ml of methanol. 12 ml of water were added to the solution and the basic solution was boiled at reflux for 16 hours under nitrogen. The solution was subsequently cooled down and extracted with a small amount of diethyl ether. The aqueous phase was then adjusted to pH 1 with 1-N aqueous phosphoric acid and ice-cooling and extracted several times with plenty of ethyl acetate. The organic phases were combined, dried over sodium sulphate and evaporated down. The oily residue was subsequently boiled with benzene and 2 hours on a water separator. After evaporation of the solvent, there was obtained an oil which could be directly further processed. For the analysis, the crude (3aR, 4S, 5R, 6aS)-4-benzyloxymethyl-hexahydro-5-hydroxy-2H-cyclopenta[b]furan-2-one was purified on a silic gel column; $[\alpha]_D^{22} = -2°$ ($c = 0.06$ in methylene chloride).

EXAMPLE 25 a. To a solution of 6 g of (3-endo-hydroxymethyl-5,6-dimethyl-5-norbornen-2-endo-yl)-methyl hydrogen phthalate in 200 ml of methanol, there is added in the cold an alcoholic diazomethane solution until the yellow colouration is permanent. After brief standing, the solvent is removed and there is obtained in quantatative yield the methyl ester of the hydrogen phthalate as a colourless oil. IR: 3526, 1731, 744 cm$^{-1}$ (liquid).

b. 5.6 g of (3-endo-hydroxymethyl-5,6-dimethyl-5-norbornen-2-endo-yl)-methyl methyl phthalate are dissolved in 48 ml of dimethyl sulphoxide. There are added with stirring 0.8 g of crystallised phosphoric acid and 10 g of dicyclohexylcarbodiimide. In so doing the temperature should not rise over 25° C. After a short time, the separation of crystalline dicyclohexylurea begins. The mixture is stirred for 5 hours at room temperature, subsequently poured onto ice water, diluted with ether and filtered. The organic phase is separated, the aqueous phase extracted once with ether and the combined organic phases washed five times with water. The mixture is dried over sodium sulphate and evaporated down. The oil thus obtained is chromatographed on Kieselgel with methylene chloride/ethyl acetate (9:1) as the eluant to completely separate the urea. There is obtained (3-endo-formyl-5,6-dimethyl-5-norbornen-2-endo-yl)-methyl methyl phthalate. IR: 2748, 1602 cm$^{-1}$ (liquid).

EXAMPLE 26

5.6 g of (3-endo-formyl-5,6-dimethyl-5-norbornen-2-endo-yl)-methyl methyl phthalate are dissolved in 9 ml of acetic anhydride. After the addition of 0.7 g of anhydrous sodium acetate, the mixture is heated for 2 hours under argon to 155° C. The cooled solution is poured into ice water, extracted twice with ethyl acetate, washed with water, dilute sodium bicarbonate solution and water, dried over sodium sulphate and evaporated down. After chromatography on Kieselgel with ether as the eluant, there is obtained (3-acetoxymethylene-5,6-dimethyl-5-norbornen-2-endo-yl)- methyl methyl phthalate. IR: 1750, 1733, 746 cm$^{-1}$ (liquid).

EXAMPLE 27

6.5 g of (3-acetoxymethylene-5,6-dimethyl- 5-norbornen-2-endo-yl)-methyl methyl phthalate are dissolved in 65 ml of methanol, 1.5 g of piperidine added thereto and the mixture heated under reflux for 1.5 hours under argon. The cooled solution is evaporated down under vacuum, the remaining oil dissolved in 400 ml of ether, mixed with 650 ml of 0.1-N sulphuric acid and stirred vigorously for 1 hour at room temperature. The organic phase is separated, the aqueous phase extracted once with ethyl acetate and the combined organic phases washed with water, dilute sodium bicarbonate solution and water. After drying over sodium sulphate and evaporating down, there is obtained (3-exo-formyl-5,6-dimethyl-5-norbornen-2-endo-yl)-methyl phthalate as a brown oil which is purified by chromatography on Kieselgel with ether as the eluant. IR: 2722, 1730, 747 cm$^{-1}$ (liquid).

EXAMPLE 28

9.4 g of (3-endo-formyl-5,6-dimethyl-5-norbornen-2-endo-yl)-methyl methyl phthalate are dissolved in 190 ml of absolute benzene. After the addition of 2 g of piperidine acetate, the mixture is heated at reflux for 5 hours under argon. The solution is diluted with 100 ml of ether and, after the addition of 900 ml of 0.1-N sulphuric acid, stirred at room temperature for a further 1 hour. The organic layer is separated, the aqueous phase extracted three times with ether, the combined organic phases washed once with bicarbonate solution, dried and evaporated down. There is obtained (3-exo-formyl-5,6-dimethyl-5-norbornen-2-endo-yl)-methyl methyl phthalate as a light yellow oil which is purified by chromatography on Kieselgel with ether/hexane (4:1) as the eluant. IR: 2722, 1730, 747 cm$^{-1}$ (liquid).

EXAMPLE 29

505 mg of sodium borohydride are dissolved in 50 ml of methanol. A solution of 10.3 g of (3-exo-formyl-5,6-dimethyl-5-norbornen-2-endo-yl)-methyl methyl phthalate in 100 ml of methanol is added dropwise thereto with ice cooling and left to stir for a further 4 hours at room temperature. The excess sodium borohydride is hydrolysed by the addition of water at 0° C and the solution is extracted three times with ethyl acetate, washed once with saturated sodium chloride solution, dried and evaporated down. There is obtained [3-exo-(hydroxymethyl)-5,6-dimethyl-5-norbornen-2-endo-yl]-methyl methyl phthalate as a colourless oil which can be purified by chromatography on Kieselgel with ether/hexane (4:1) as the eluant. IR: 3528, 1729, 744 cm$^{-1}$ (liquid).

EXAMPLE 30

3.3 g of [3-exo-(hydroxymethyl)-5,6-dimethyl-5-norbornen-2-endo-yl]-methyl methyl phthalate are dissolved in 50 ml of absolute ether and there are added at room temperature 1.6 g of dihydropyran and a few mg of p-toluenesulphonic acid. After brief stirring, the mixture is left to stand under anhydrous conditions overnight. Some potassium hydroxide platelets are added to the solution which is then shaken well, decanted off and evaporated down. The oily 5,6-dimethyl-3-exo-[(tetrahydro-2H-pyran-2-yl)-oxymethyl]-5-norbornen-2-endo-yl-methyl methyl phthalate thus obtained can be further reacted without additional purification. IR: 1731, 1077, 746 cm$^{116\ 1}$ (liquid).

EXAMPLE 31

12.7 g of 5,6-dimethyl-3-exo[(tetrahydro-2H-pyran-2-yl)-oxymethyl]-5-norbornen-2-endo-yl-methyl methyl phthalate are dissolved in 100 ml of methanol and a solution of 11 g of potassium hydroxide in 50 ml of water and 50 ml of methanol added thereto. After stirring for 16 hours at room temperature, the bulk of the alcohol is evaporated off, the mixture diluted with water and extracted several times with ethyl acetate. The organic phase is washed with saturated sodium chloride solution and dried over sodium sulphate/potassium carbonate. After evaporating down, there is obtained 5,6-dimethyl-3-exo-[(tetrahydro-2H-pyran-2yl)-oxymethyl]-5-norbornen-2-endomethanol as an oil. IR: 3448, 1665, 1062, 1028 cm$^{-1}$ (liquid).

EXAMPLE 32

29.3 g of 5,6-dimethyl-3-exo[(tetrahydro-2H-pyran-2-yl)-oxymethyl]-5-norbornen-2-endo-methanol are dissolved in 325 ml of absolute pyridine. There are slowly added dropwise thereto at 0° C with stirring 18.4 g of methane sulphochloride and the mixture is stirred for a further 6 hours at the same temperature. Thereafter the mixture is poured onto ice, extracted three times with 200 ml of ether, the organic phase washed twice with saturated sodium chloride solution, dried over sodium sulphate and evaporated down. The oil thus obtained is filtered through a short Kieselgel column using absolute ether as the eluant and yields 5,6-dimethyl-3-exo-(tetrahydro-2H-pyran-2-yl)-oxymethyl-5-norbornen-2-endo-yl-methyl methanesulphonate. IR: 1357, 1179, 1028 cm$^{-1}$ (liquid).

EXAMPLE 33

10.5 g of well-dried sodium cyanide are dissolved with gentle warming in 185 ml of absolute dimethyl sulphoxide. A solution of 15.0 g of 5,6-dimethyl-3-exo-(tetrahydro-2H-pyran-2-yl)-oxymethyl-5-norbornen-2-endo-yl-methyl methanesulphonate in 75 ml of absolute dimethylsulphoxide is slowly added dropwise thereto at 60° C with vigorous stirring. The mixture is subsequently warmed to 90° C and stirred at this temperature for 16 hours. After cooling, the mixture is poured onto ice and extracted three times with 200 ml of ether each time. The organic phase is washed five times with 100 ml of water each time, dried over sodium sulphate and evaporated down. There is obtained 5,6-dimethyl-3-exo-(tetrahydropyran-2-yl)-oxymethyl-5-norbornen-2-endo-acetonitrile as an oil which is processed further without further purification. IR: 2248, 1037 cm$^{-1}$ (liquid).

EXAMPLE 34

11.5 g of 5,6-dimethyl-3-exo-(tetrahydropyran-2-yl)-oxymethyl-5-norbornen-2-endo-acetonitrile are dissolved in 50 ml of methanol and 14 ml of 3-N hydrochloric acid added thereto. The mixture is stirred overnight at room temperature, heated at reflux for a further 2 hours, extracted several times with ethyl acetate, washed with dilute bicarbonate solution, dried and evaporated down. After chromatography on Kieselgel with ether/hexane (4:1) as the eluant, there is obtained 3-exo-(hydroxymethyl)-5,6-dimethyl-5-norbornen-2-endo-acetonitrile as an oil. IR: 3446, 2248, 1052 cm$^{-1}$ (liquid).

EXAMPLE 35

6.8 g of 55% sodium hydride (freed from adhering mineral oil by washing three times with absolute monoglyme) are suspended in 100 ml of absolute monoglyme and 7.6 g of 3-exo-(hydroxymethyl)-5,6-dimethyl-5-norbornen-2-endo-acetonitrile in 50 ml of monoglyme are added thereto. The mixture is stirred at room temperature for 15 minutes and subsequently a solution of 18.8 g of benzyl chloride in 30 ml of monoglyme is added dropwise thereto. After heating for 3 hours at 90° C, the mixture is mixed in the cold with 50 ml of water, extracted with ethyl acetate, dried and evaporated down. After chromatography on Kieselgel with ether/hexane (4:1) as the eluant, there is obtained 3-exo-(benzyloxy)-methyl-5,6-dimethyl-5-norbornen-2-endo-acetonitrile as an oil. IR: 2246, 1496, 1097, 737, 696 cm$^{-1}$ (liquid).

EXAMPLE 36

1.0 g of 3-exo-(benzyloxy)-methyl-5,6-dimethyl-5-norbornen-2-endo-acetonitrile are dissolved in 40 ml of methylene chloride and ozonised at −70° C. The end of the reaction is indicated by iodine separation in a washing bottle attached behind the reaction vessel with 10% potassium iodide/starch solution. The excess ozone is removed in an argon stream. 5 ml of dimethyl sulphide are added at −20° C, the mixture allowed to stir for 1 hour at −20° C and for 1 hour at 0° C and evaporated down. There is obtained 3α,5α-diacetyl-2β-benzyloxymethyl-1α-cyclopentane-acetonitrile as an oil which is subjected directly to the Baeyer-Villiger oxidation without further purification. IR: 2248, 1713, 1106, 743 cm$^{-1}$ (liquid).

EXAMPLE 37

6.5 ml of trifluoroacetic anhydride are slowly added dropwise at 0° C with stirring to a mixture of 1.04 ml of 90% hydrogen peroxide in 20 ml of methylene chloride. Then the mixture is left to stir for a further 10 minutes at room temperature. This solution of trifluoroperacetic acid is added dropwise with vigorous stirring to a suspension of 11.2 g of disodium hydrogen phosphate, 600 mg of 3α,5α-diacetyl-2β-benzyloxymethyl-1α-cyclopentane-acetonitrile and 30 ml of methylene chloride. The dropping rate of the peracid is regulated so that the mixture boils gently at reflux. After 2 hours, the mixture is filtered, rinsed well with methylene chloride and evaporated down. After chromatography on Kieselgel with ether as the eluant there is obtained 4,4-benzyloxymethyl-5α-cyanomethyl-1α,3α-cyclopentylene diacetate as an oil. IR: 2250, 1740, 1240, 742 cm$^{-1}$ (liquid).

EXAMPLE 38

250 mg of 4,4-benzyloxymethyl-5α-cyanomethyl-1α,3α-cyclopentylene diacetate are dissolved in 10 ml of methanol, mixed with a mixture of 620 mg of potassium hydroxide in 5 ml of methanol and 5 ml of water and boiled at reflux overnight. The alkaline solution is extracted once with ether, subsequently acidified at 0° C with 2-N phosphoric acid and, after saturation with solid sodium chloride, extracted five times with ethyl acetate. The mixture is dried over sodium sulphate and evaporated down. To complete the lactonisation, the obtained oil is dissolved in 50 ml of absolute benzene, boiled at reflux for 2 hours and the solvent distilled off. By means of preparative thin-layer chromatography on Kieselgel with ethyl acetate as the eluant, there is obtained (3αH, 6αH)-4α-benzyloxymethyl-hexahydro-5β-hydroxy-2H-cyclopenta-b-furan-2-one as a colorless oil. IR: 3454, 1773, 1100, 743, 700 cm$^{-1}$ (liquid).

EXAMPLE 39

20 g of 5,6-dimethyl-bicyclo[2.2.1]hept-5-en-2-endo,3-endo-dimethanol are dissolved in 50 ml of absolute benzene and 55.6 ml of absolute pyridine are added thereto. A solution of 9.03 g of acetyl chloride in 16 ml of absolute benzene is slowly added dropwise thereto at 0° C with stirring and the mixture left to stir for a further 2 hours. Then the mixture is poured onto ice/3-N hydrochloric acid, extracted three times with ethyl acetate, washed once with dilute soda solution, dried over sodium sulphate and evaporated down. There is obtained an oily mixture (25.6 g) of monoacetate, diacetate and starting material, which can be easily separated into the individual components by a single chromatography on Kieselgel with methylene chloride-/ethyl acetate (9:1) as the eluant. The yield of monoacetate comes to 11.5 g. The diacetate is saponified to the starting material with methanolic potassium hydroxide. IR: 3456, 1741, 1667 cm$^{-1}$ (liquid).

EXAMPLE 40

8.5 g of [3-endo-(hydroxymethyl)-5,6-dimethyl-5-rorbornen-2-endo-yl]-methyl acetate are dissolved in a mixture of 45 ml of ethyl acetate and 45 ml of absolute dimethyl sulphoxide. 3.6 g of pyridine trifluoroacetate and 25.4 g of dicyclohexylcarbodiimide are added thereto at room temperature with stirring. Room temperature is maintained by cooling with an ice bath. After stirring for 5 hours at room temperature, the mixture is poured onto ice water, diluted with 100 ml of ether and the precipitated dicyclohexylurea filtered off. The ethereal phase is separated, the aqueous phase extracted once with ether, the organic phases combined, washed five times with water, dried over sodium sulphate and evaporated down. The residual dicyclohexylurea can be separated by chromatography on Kieselgel with methylene chloride/ethyl acetate (9:1) as the eluant. There is obtained (3-endo-formyl-5,6-dimethyl-5-norbornen-2-endo-yl)-methyl acetate: IR: 2744, 2720, 1745, 1720 cm$^{-1}$ (liquid).

EXAMPLE 41

7.5 g of (3-endo-formyl-5,6-dimethyl-5-norbornen-2-endo-yl)-methyl acetate was dissolved in 150 ml of absolute benzene. 4.9 g of piperidine acetate are added thereto and the mixture boiled at reflux overnight under argon. The mixture is mixed with 140 ml of ether and 750 ml of sulphuric acid and stirred at room temperature for 1 hour. Subsequently the organic phase is separated, the aqueous phase extracted three times with ether, the combined organic solutions washed once with 50 ml of dilute bicarbonate solution, dried and evaporated down. After chromatography on Kieselgel with methylene chloride/ethyl acetate (9:1), there is obtained (3-exo-formyl-5,6-dimethyl-5-norbornen-2-endo-yl)-methyl acetate as an oil. IR: 2714, 1742, 1720 cm$^{-1}$ (liquid).

EXAMPLE 42

2.0 g of sodium borohydride are dissolved in 150 ml of methanol. A solution of 32.2 g of 3-exo-formyl-5,6-dimethyl-5-norbornen-2-endo-yl-methyl acetate in 200 ml of methanol are added dropwise thereto at 0° C. By the dropwise addition of 1-N sulphuric acid the pH value of the mixture is held at 7. After 1 hour, the excess borohydride is decomposed with several ml of water, the mixture is extracted with ether/ethyl acetate, dried over sodium sulphate and the solvent evaporated. After chromatography on Kieselgel with ether/hexane (4:1) as the eluant, there is obtained (3-exo-hydroxymethyl-5,6-dimethyl-5-norbornen-2-endo-yl)-methyl acetate as an oil. IR: 3440, 1743, 1056, 1032 cm$^{-1}$ (liquid).

EXAMPLE 43

26 g of (3-exo-hydroxymethyl-5,6-dimethyl-5-norbornen-2-endo-yl)-methyl acetate are dissolved in 100 ml of absolute ether and 19.2 g of dihydropyran added thereto. After the addition of several mg of p-toluenesulphonic acid, the mixture is stirred for 10 minutes and left to stand overnight at room temperature. The mixture is neutralised with several pellets of solid potassium hydroxide, decanted off and evaporated down. There is obtained [5,6-dimethyl-3-exo-(tetrahydro-2H-pyran-2-yl)-oxymethyl-5-norbornen-2-endo-yl]-methyl acetate.

EXAMPLE 44

35.8 g of [5,6-dimethyl-3-exo-(tetrahydro-2H-pyran-2-yl)-oxymethyl-5-norbornen-2-endo-yl]-methyl acetate are dissolved in 150 ml of methanol and a solution of 32 g of potassium hydroxide in 150 ml of water and 100 ml of methanol added thereto. After stirring for 6 hours at room temperature, the methanol is evaporated off, the mixture extracted three times with ethyl acetate, dried over sodium sulphate and evaporated down. There are obtained 33.7 g of a colourless oil which is purified by chromatography on Kieselgel with absolute ether as the eluant. There is obtained 5,6-dimethyl-2-endo-hydroxymethyl-3-exo-(tetrahydro-2H-pyran-2-yl)-oxymethyl-5-norbornene. IR: 3448, 1665, 1062, 1028 cm$^{-1}$ (liquid).

We claim:
1. A compound of the formula

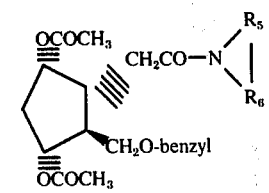

wherein $R_5$ and $R_6$ are lower alkyl, which taken together form a pyrrolidinyl ring.

2. The compound of claim 1 wherein said compound is (1S, 3R,4S,5R)-4-benzyloxymethyl-5-[(1-pyrrolidinyl-carbonyl)-methyl]-1,3-cyclopentylene-diacetate.

* * * * *